US008927263B2

(12) United States Patent
Smart et al.

(10) Patent No.: US 8,927,263 B2
(45) Date of Patent: Jan. 6, 2015

(54) DERIVATIZATION OF PNGASE F RELEASED GLYCANS ON AN HPLC CHIP

(71) Applicant: Agilent Technologies, Inc., Loveland, CO (US)

(72) Inventors: Brian Phillip Smart, San Jose, CA (US); Magdalena Anna Ostrowski, Mountain View, CA (US); Gregory Staples, San Francisco, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 0 days.

(21) Appl. No.: 13/953,105

(22) Filed: Jul. 29, 2013

(65) Prior Publication Data
US 2014/0038215 A1 Feb. 6, 2014

Related U.S. Application Data

(60) Provisional application No. 61/677,874, filed on Jul. 31, 2012.

(51) Int. Cl.
C12Q 1/34 (2006.01)
G01N 30/60 (2006.01)
G01N 30/88 (2006.01)

(52) U.S. Cl.
CPC ............ C12Q 1/34 (2013.01); G01N 2333/924 (2013.01); G01N 2030/8818 (2013.01); G01N 30/6095 (2013.01); G01N 2400/38 (2013.01); G01N 2400/12 (2013.01)
USPC ........................................ 435/288.6; 435/18

(58) Field of Classification Search
CPC ................. C12Q 1/34; G01N 30/6095; G01N 2030/8818; G01N 2333/924; G01N 2400/12; G01N 2400/38
See application file for complete search history.

(56) References Cited

U.S. PATENT DOCUMENTS 5,283,353 A * 2/1994 Rasmussen et al. ......... 536/17.2
2009/0258437 A1 * 10/2009 Baginski ........................ 436/501
2010/0190146 A1 7/2010 Bynum et al.

OTHER PUBLICATIONS

Hase, S., Precolumn derivatization for chromatographic and electrophoretic analyses of carbohydrates, J. Chromatography A, 1996, 720(1-2): p. 173-182.
Rasmussen, J.R. et al., Identification and Derivatization of (Oligosaccharyl)Amines Obtained by Treatment of Asparagine-Linked Glycopeptides with N-Glycanase Enzyme, Journal of the American Chemical Society, 1992, 114(3): p. 1124-1 126.
Inagaki, S. et al., Highly sensitive and positively charged precolumn derivatization reagent for amines and amino adds in liquid chromatography/electrospray ionization tandem mass spectrometry, Rapid Communications in Mass Spectrometry, 2010, 24(9): p. 1358-1364.

* cited by examiner

Primary Examiner — Jon P Weber
Assistant Examiner — Robert Yamasaki

(57) ABSTRACT

A microfluidic device for glycan analysis includes a deglycosylation column comprising a glycosidase attached to a solid support; a tagging column comprising a reactive ester for reaction with an amino group, wherein the tagging column is arranged downstream of the deglycosylation column; an analytical column comprising a stationary phase capable of separating a derivatized glycan; and a plurality of inlet/outlet ports configured to connect with channels on a switching element to form flow paths.

19 Claims, 5 Drawing Sheets

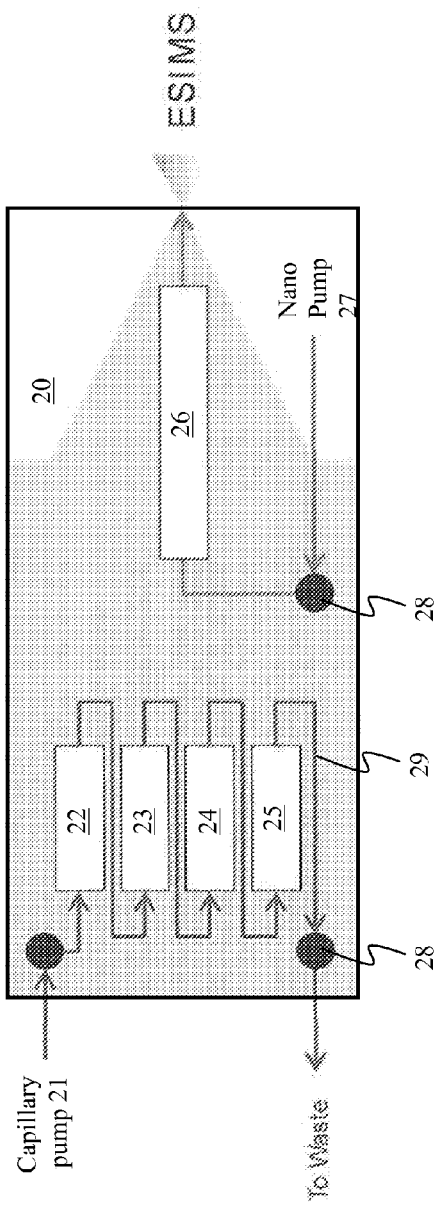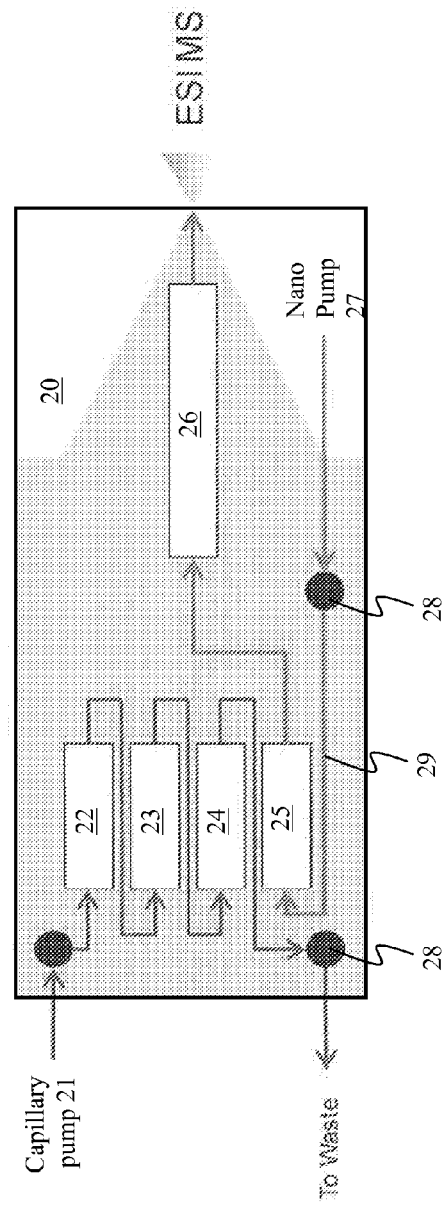
FIG. 2(A)
FIG. 2(B)

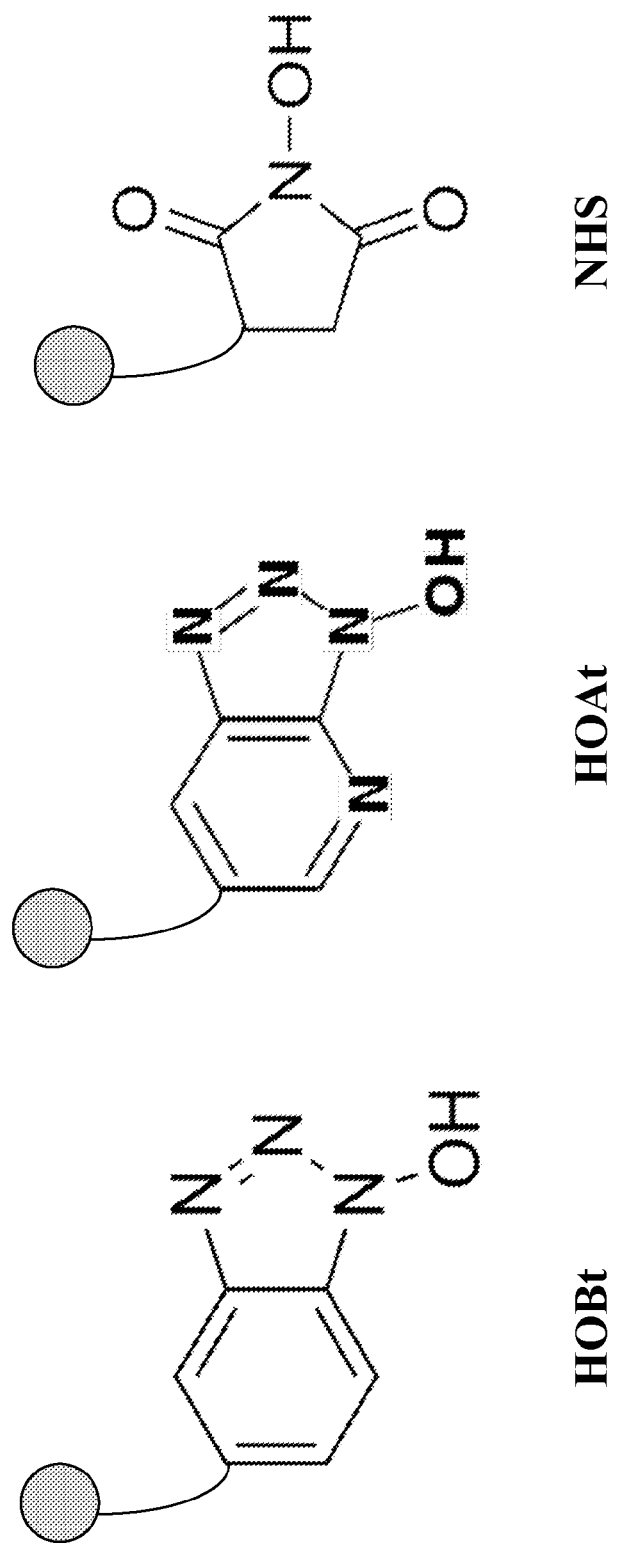

DERIVATIZATION OF PNGASE F RELEASED GLYCANS ON AN HPLC CHIP

PRIORITY CLAIMS AND RELATED PATENT APPLICATIONS

This application claims the benefit of priority from U.S. Provisional Application Ser. No. 61/677,874, filed on Jul. 31, 2012, the entire content of which is incorporated herein by reference in its entirety.

FIELD OF THE INVENTION

The present invention relates to the analysis of glycans from glycoproteins, particularly analysis of glycans using microfluidic devices.

BACKGROUND OF THE INVENTION

Glycosylation is the most common post-translational modification of cell surface and extracellular matrix proteins. The glycoprotein glycans expressed by a given organism comprise complex mixtures reflective of the non-template driven biosynthesis of these posttranslational modifications. The mixtures contain components that, while physiologically relevant, represent a small fraction of the total glycan population. Thus, characterization of glycoproteins has been a challenging task.

Glycoproteins play important roles in many cellular functions, such as cell-adhesion and immune responses. Changes in glycan profiles have been correlated with altered physiological conditions and disease states, such as cancer and rheumatoid arthritis. Therefore, the ability to detect and quantify the glycan components is important.

Glycoproteins may be glycosylated at different glycosylation sites (glycosites). Glycosylation typically occurs at asparagine (N-glycosylation) or serine (O-glycosylation) residues of the glycosites. In addition, at any particular glycosite, different glycans (oligosaccharides) may be attached to that particular glycosite. This structural heterogeneity complicates the study of glycoproteins, particularly the carbohydrates attached to the glycoproteins. Complicating glycan heterogeneity is the fact that the amount of glycoprotein sample available for analysis from biological sources is often limited. For these reasons, mass spectrometry, which is both highly sensitive and able to characterize complex mixtures of compounds, has emerged as the ideal technology for glycan analysis. Unfortunately, glycans have inherently low ionization efficiency.

Because of this, many researchers have attempted to derivatize glycans with chemical compounds that can increase ionization efficiency (see, Hase, S., *Precolumn derivatization for chromatographic and electrophoretic analyses of carbohydrates*, J. Chromatography A, 1996, 720 (1-2): p. 173-182). The most common "tagging" method is reductive amination of the free reducing end (i.e., the open ring aldehyde form) of the glycan with an aromatic compound containing a primary amine. These workflows require addition of reducing agents, the most common of which is sodium cyanoborohydride, in order to stabilize the imine formed during the derivatization reaction. Thus, these strategies involve significant sample handling and purification steps, which increases the likelihood that valuable analyte may be lost.

However, as in reductive amination approaches, the sample preparation and amount of sample handling needed to utilize the R-glycosylamine intermediates for derivatization chemistry are significant, and not compatible with high throughput glycan analysis. Thus, there are currently no experimental protocols that combine the benefits of glycan derivatization (increased ionization efficiency) with rapid sample preparation or minimal sample manipulation.

SUMMARY OF THE INVENTION

One aspect of the invention relates to microfluidic devices for glycan analysis. A microfluidic device in accordance with one embodiment of the invention includes a deglycosylation column comprising a glycosidase attached to a solid support; a tagging column comprising a reactive ester for reaction with an amino group, wherein the tagging column is arranged downstream of the deglycosylation column; an analytical column comprising a stationary phase capable of separating a derivatized glycan; and a plurality of inlet/outlet ports configured to connect with channels on a switching element to form flow paths.

In accordance with embodiments of the invention, the glycosidase may be PNGase F or PNGase A.

In accordance with some embodiments of the invention, any one of the above microfluidic devices may further comprise a clean-up column having a stationary phase capable of binding a protein, wherein the clean-up column is arranged downstream of the deglycosylation column and upstream of the tagging column. The clean-up column may comprise a reversed phase stationary phase.

In accordance with some embodiments of the invention, any one of the above microfluidic devices may further comprise a trapping column having a stationary phase capable of binding the derivatized glycan, wherein the trapping column is configured to be connected downstream of the tagging column and upstream of the analytical column. The trapping column may comprise a reversed phase stationary phase.

Another aspect of the invention relates to a system for analyzing a sample, which may comprise any one of the above microfluidic device, a switching device, and a mass spectrometer.

Another aspect of the invention relates to methods for glycan analysis. A method in accordance with one embodiment of the invention includes: applying a sample comprising a glycoprotein to the deglycosylation column on the microfluidic device to produce a deglycosylated mixture; passing the deglycosylated mixture through the tagging column to produce a derivatized glycosylamine; and separating the derivatized glycosylamine on the analytical column.

In accordance with embodiments of the invention, in any of the methods described above, the glycosidase may be PNGase F or PNGase A.

In accordance with some methods of the invention, any one of the above microfluidic devices may further comprise a clean-up column having a stationary phase capable of binding a protein, wherein the clean-up column is arranged downstream of the deglycosylation column and upstream of the tagging column. The clean-up column may comprise a reversed phase stationary phase. The method further comprises passing the deglycosylated mixture through the clean-up column before the passing the deglycosylated mixture through the tagging column.

In accordance with some methods of the invention, any one of the above microfluidic devices may further comprise a trapping column having a stationary phase capable of binding the derivatized glycan, wherein the trapping column is configured to be connected downstream of the tagging column and upstream of the analytical column. The trapping column may comprise a reversed phase stationary phase. The method further comprises passing the derivatized glycan through the trapping column before the separating the derivatized glycosylamine on the analytical column.

Other aspects and advantages of the invention will be apparent from the following description and the appended claims.

BRIEF DESCRIPTION OF DRAWINGS

FIG. 2A shows a microfluidic device of the invention, illustrating a deglycosylation reaction and tagging reaction.

FIG. 2B shows a microfluidic device of the invention, illustrating analysis of a derivatized glycan.

FIG. 5 shows other examples of activated esters that may be used with embodiments of the invention.

DEFINITIONS

Figure 1:
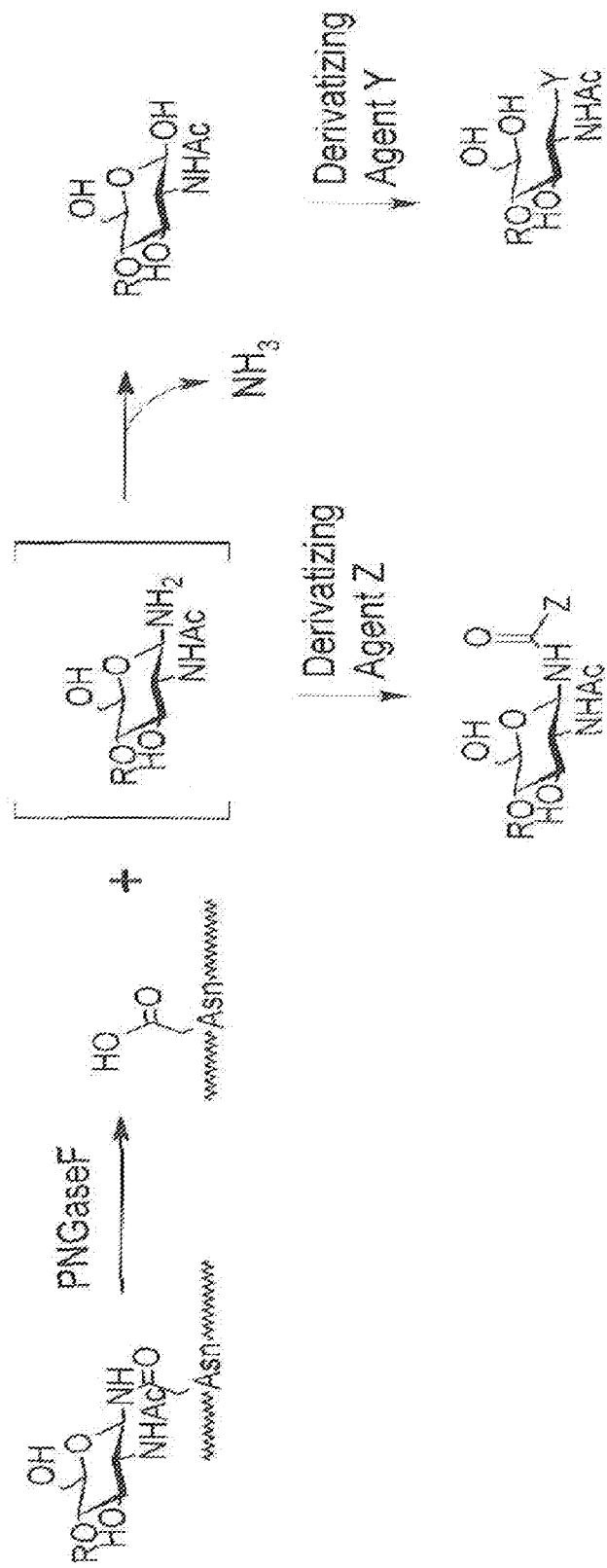
FIG. 1 shows a reaction mechanism for deglycosylation and derivatization of a glycosylamine or a glycan.

As used herein, the term "microfluidic device" refers a device having chambers and/or channels of micron or submicron dimensions that allow passage of fluid. The chambers or channels are generally from 1 µm to less than 1000 µm in diameter (or, if not circular, the largest dimension of the cross section), such as 1 µm to 500 µm, 10 µm to 300 µm, 50 µm to 250 µm, by way of examples.

As used herein, the term "deglycosylation column" or "enzyme reactor" refers to a microfluidic column/channel containing a glycosidase attached to a solid support.

As used herein, the term "clean-up column" refers to a microfluidic column/channel for binding proteins or peptides such that the proteins or peptides may be separated from glycans after the deglycosylation reaction. The clean-up column may comprise a stationary phase, to which the proteins or peptides can bind, such as a reversed phase or PGC stationary phase.

As used herein, the term "tagging column" or "derivatization column" refers to a microfluidic column/channel containing a reactive ester attached to a solid support. The reactive ester is capable of reacting with an amino group of a glycosylamine. The reactive esters (or activated esters), for example, may comprise a phenol ester, an HOBt ester, an HOAt ester, or an NHS ester as discussed in more detail in this description.

As used herein, the term "trapping column" refers to a column on a microfluidic device having a stationary phase for binding the derivatized glycans such that they can be separated from other components. For glycans that have been derivatized with a hydrophobic group, the trapping column may comprise a PGC or reversed phase stationary phase, wherein the reversed phase stationary phase may be polymer-based or silica-based. Any reversed phase stationary phase known in the art may be used, such as C-1, C-4, C-8, and C-18.

As used herein, the term "analytical column" refers to a column on a microfluidic device having a stationary phase for separating derivatized glycans. The "analytical column" may separate the derivatized glycans by electrophoresis or liquid chromatography (LC), particularly HPLC. Examples of HPLC "analytical column" for use in embodiments of the invention include columns having a PGC or reversed phase stationary phase, wherein the reversed phase stationary phase may be polymer-based or silica-based. Any reversed phase stationary phase known in the art may be used, such as C-1, C-4, C-8, and C-18.

DETAILED DESCRIPTION OF THE INVENTION

As noted above, the current strategies for derivatization of PNGase F released N-glycans rely on solution-phase approaches, in which amine-containing components are reacted with the reducing ends of the glycans, followed by reduction (using sodium cyanoborohydride) of the imine products. These approaches involve significant amounts of sample manipulations. In addition, excess tagging reagents need to be removed prior to LC/MS analysis. These solution based approaches involve significant amounts of time for both glycan release and glycan derivatization, which severely decreases the throughput of glycan analyses.

The release of N-linked glycans from glycoproteins by glycosidases (e.g., PNGase F) presents a unique opportunity for glycan tagging, as the enzyme liberates glycans as reducing end β-glycosylamines. The free amino group on β-glycosylamines possess reactivity ideal for derivatization reactions. β-glycosylamines, however, are short-lived; they are readily hydrolyzed to produce glycans having free reducing ends. In typical solution-phase experiments that utilize PNGase F, which are normally allowed to proceed for about 16 hours, the β-glycosylamine intermediate is completely converted to the free reducing end form. For these reasons, it is not surprising that only one report has documented the use of this short-lived reducing end chemistry for glycan tagging (Rasmussen, J. R. et al., *Identification and Derivatization of (Oligosaccharyl)Amines Obtained by Treatment of Asparagine-Linked Glycopeptides with N-Glycanase Enzyme*, Journal of the American Chemical Society, 1992, 114(3): p. 1124-1126).

The fact that the β-glycosylamine intermediate is short-lived makes it difficult to use this intermediate in the characterization of glycans using the conventional solution based approaches. Recently, Bynum et al. disclosed a microfluidic device for analyzing carbohydrates released from glycoproteins (U.S. Patent Application Publication No. 2010/0190146, the disclosure of which is incorporated by reference in its entirety). This microfluidic device is efficient and convenient for the analysis of carbohydrates released from glycoproteins. Importantly, these microfluidic devices contain immobilized glycosidases that have been shown to be very efficient in glycan cleavages from glycoproteins. The efficient cleavages make it easier to detect the β-glycosylamine intermediates.

The device disclosed in the '146 application is similar to the Agilent mAb-Glyco Chip, which is designed for on-chip deglycosylation of monoclonal antibodies (mAbs) as well as subsequent on-chip enrichment, separation and MS based detection of cleaved N-glycans with an Agilent HPLC-Chip/MS system. Deglycosylation is based on an integrated immobilized PNGase F enzyme reactor column (Agilent Technologies, Santa Clara, Calif.). Embodiments of the invention relate to microfluidic chips for analysis of glycans released from glycoproteins. Microfluidic chips of the invention are similar to the mAb-Glyco Chip from Agilent Technologies, Inc. (Santa Clara, Calif.) and similar to the microfluidic devices disclosed in the '146 application. However, microfluidic devices of the invention incorporate unique glycan derivatization columns to facilitate the characterization of the glycans.

Some embodiments of the invention relate to methods for analysis of glycans released from glycoproteins, using microfluidic chips of the invention. These methods combine online enzymatic glycan release reactions with novel, rapid (fast enough to allow tagging of β-glycosylamine intermediates) derivatizations to provide tagged glycans for improved MS detection. This strategy includes the benefits of glycan tagging, as demonstrated in the conventional solution-phase approaches, while eliminating the manual sample handling steps and maximizing the throughputs.

FIG. 1 shows a schematic illustrating a deglycosylation reaction by a glycosidase (e.g., PNGase F). As shown, the glycan is removed from the asparagine residue by cleavage of the amide bond, resulting in the formation of a β-glycosylamine. The β-glycosylamine has a primary amino group (—NH$_2$) that can be used for derivatization, as shown in reaction with Agent Z having a reactive acyl group. The reaction between Agent Z and the amino group forms an amide derivative. By proper selection of the group on Agent Z, one can improve the properties of the glycans for analysis. For example, one may select an Agent Z containing a hydrophobic group to facilitate the separation and/or analysis of the glycans using HPLC and MS.

FIG. 1 also shows that the β-glycosylamine is not stable and is eventually hydrolyzed in solution to release the amino group from the glycosylamine, leading to the formation of a regular carbohydrate. The carbohydrate has a reducing end (an aldehyde group when in open form) that can be used to form a derivative with Agent Y, which typically contains an amino group for the formation of an imine (Schiff base) with the reducing sugar (i.e., the aldehyde group). The initial imine product is not very stable. Therefore, in the conventional approach, the imine is reduced with sodium cyanoborohydride to produce an amino group, as noted in the above discussion.

It is clear from FIG. 1 that if one can take advantage of the reactivity of the amino (—NH$_2$) group on the initial β-glycosylamine product, the derivatization reactions would be simpler. Embodiments of the invention are based on this type of derivatization reactions. In addition, embodiments of the invention make use of microfluidic devices. It has been shown that deglycosylation reactions are surprisingly more efficient in microfluidic devices using immobilized glycosidases (see, Bynum et al., U.S. Patent Application Publication No. 2010/0190146). By using microfluidic devices, one can also minimize the amounts of samples needed for analysis and avoid the tedious manual operations.

Some embodiments of the invention relate to microfluidic devices for deglycosylation of glycoproteins and derivatization of the released glycans to facilitate glycan analysis. FIG. 2A and 2B show an example of a microfluidic device of the invention and its operation. As shown in FIG. 2A, a microfluidic device 20 comprises several columns 22-26 and a plurality of inlet/outlet ports 28. The inlet/outlet ports 28 are configured to connect with different channels 29 on one or more switching devices to form different flow paths.

A microfluidic chip of the invention may be based on modification of the mAb-Glyco-Chip available from Agilent Technologies, Inc. (Santa Clara, Calif.). The modification comprises the addition of a channel/column that contains a glycan tagging reagent, which may be immobilized to a solid phase, as shown in FIGS. 2A and 2B. A microfluidic chip of the invention may have two operating modes; sample preparation (FIG. 2A) and sample analysis (FIG. 2B).

As shown in FIG. 2A, in the sample preparation mode, a glycoprotein sample is pumped into the microfluidic chip 20 by a capillary pump 21 (or a similar device). The glycoprotein sample first enters the deglycosylation column (or enzyme reactor) 22, where it is deglycosylated by the immobilized glycosidase (e.g., PNGase F).

In accordance with embodiments of the invention, the deglycosylation column (enzyme reactor) 22 may comprise a solid support, to which a deglycosylation enzyme is attached. The deglycosylation enzyme is capable of cleaving carbohydrates from a glycoprotein. In most glycoproteins, the carbohydrate moiety is attached to the nitrogen of the β-amide group in an asparagine residue (N-linked glycans) or to the oxygen of the hydroxyl group in a serine or threonine residue (O-linked glycans). Embodiments of the invention relate to N-linked glycans.

Any enzyme that can cleave the N-linked glycans from glycoproteins (i.e., N-glycanase) may be used in the present invention. These enzymes are known in the art and include, but are not limited to, PNGase A and PNGase F. Preferred embodiments of the invention may use PNGase F. Immobilized PNGase F has been shown to be very efficient in glycan cleavage from glycoproteins and the reactions are typically complete within a few seconds to a few minutes (see, Bynum et al., U.S. Patent Application Publication No. 2010/0190146, the disclosure of which is incorporated by reference in its entirety).

Materials and methods for immobilizing proteins to solid supports are known in the art. The solid support in the deglycosylation column (enzyme reactor) 22 may be glass or polymer beads, or a monolithic medium (such as polymethacrylate, polystyrene, polyacrylamide, or the like). Examples of making immobilized glycosidase columns may be found in U.S. Patent Application Publication No. 2010/0190146, by Bynum et al., which discloses similar deglycosylation columns. The disclosure of the application is incorporated by reference in its entirety.

After deglycosylation, the proteins may be optionally separated from the glycans by removing the proteins using a clean-up column 23. The clean-up column 23 may contain a stationary phase for binding peptides or proteins. Such stationary phase may be a reversed phase or porous graphitized carbon (PGC). Preferred embodiments of the invention may use a clean-up column 23 that contains a reversed phase stationary phase, such as C-1, C-4, C-8, or C-18 column. The clean-up column 22 may bind both deglycosylated proteins and the intact glycoproteins (due to incomplete deglycosylation reaction). The free glycans are hydrophilic and will not be retained by such clean-up columns.

The free glycans that flow through the clean-up column 23 are exposed to a channel/column 24 containing an amino reactive reagent for the derivatization of the glycosylamine. This column 24 may be referred to as a tagging column 24. The tagging reaction is possible because the enzyme reactor 22 is very efficient and can produce quantitative cleavage within a very short duration (e.g., from a few seconds to a few minutes). The fast and efficient cleavage of the glycans from the glycoproteins allows the relatively unstable glycosylamine to reach the tagging column 24 before the glycosylamines are hydrolyzed to the corresponding reducing sugars.

In accordance with embodiments of the invention, the tagging columns 24 contain amino-reactive reagents that are preferably reactive esters. The "reactive esters" or "activated esters" may comprise substituted phenol esters, NHS esters, HOBt esters, HOAt esters, or the like. In accordance with embodiments of the invention, such amino-reactive reagents may be bound to solid supports in the tagging columns 24.

After reaction, the glycosylamines are tagged with a moiety that would facilitate the separation and detection of the glycosylamine derivatives by HPLC and MS.

Next, the tagged glycans may be optionally sequestered on a trapping column 25, while any contaminants in the sample are washed away to waste. The trapping column 25 may contain a stationary phase selected for binding with the derivatized glycan (e.g., binding to the tag moiety). For example, if the tag moiety contains a hydrophobic group, the trapping column 25 may contain a reversed phase or PGC stationary phase. For hydrophobic tag moieties, it is preferred that the stationary phase contains a reversed phase, such as C-1, C-4, C-8, or C-18.

Once the tagged glycan is trapped on the trapping column 25, it may be further separated on a separation/analytical column 26 and then sent to a mass spectrometer for analysis. As shown in FIG. 2B, the microfluidic chip is switched to the analysis mode. The switching may be accomplished by rotating a switching element (or a rotor) (not shown) that contains channels 29 to connect with different inlet/outlet ports 28 on the microfluidic chip 20.

An inlet/outlet port (or "port") 28 can be a hole, orifice, opening, or a combination of the above connected to a conduit (especially a short conduit), or the like, as long as the port allows fluid to pass from one end of the port to the other. The ports 28 can be used to connect different columns on the device (different columns 22-26) at different stages when the microchip 20 is aligned with and coupled to appropriate channels 29 on a rotor or switch (not shown). For example, the microchip can be fit on top of an inner rotor and an outer rotor, as in Agilent mAb-Glyco chip. The inner and/or outer rotors can be rotated so that different ports in microchip are connected by channels in the rotor. The different channels in the rotor connect with different ports to form different flow paths. Thus, in combination with the channels on a rotor/switch, the inlet/outlet ports on the microchip can provide different flow paths to connect or disconnect different columns. The uses of such rotors/switches in microfluidic devices are known in the art, see for example the operations of Agilent mAb-Glyco chip and U.S. Patent Application Publication No. 2010/0190146, the disclosure of which is incorporated herein by reference.

Although a rotor is described above as a switching element to change the fluid communication state of the columns in the microfluidic device, other switching elements (switches) may be used without departing from the scope of the invention. For example, a set of channels and valves can be used with the microfluidic device such that different columns may be put in the flow paths at different states.

As shown in FIG. 2B, after switching, the microfluidic chip 20 is now in the analysis mode, in which the trapping column 25 is in fluid communication with the analytical column 26. A nano pump 27 may be used to generate a gradient mobile phase to perform the separation. The tagged glycans move from the trapping column 25 to the analytical column 26, where they are separated before introduction into the MS system. While an electrospray ionization (ESI) MS is shown, one skilled in the art would appreciate that other mass spectrometers may be used without departing from the scope of the invention.

As illustrated in FIGS. 2A and 2B, glycan derivatization may be performed in a column integrated into a microfluidic chip of the invention. The derivatization may increase the ionization efficiency of the glycans to facilitate their detection by mass spectrometry.

As shown in FIG. 1, a reactive Agent Z for derivatization of glycosylamines may be an acyl derivative, which may include acyl halides, anhydrides, reactive esters, etc. However, for use with embodiments of the invention, such reactive reagents should be stable (at least for a period of time) in an aqueous environment. Therefore, preferred embodiments of the invention may use active esters that can react with amines and are relatively stable in the aqueous environment. Various reactive ester types are known in the art, such as phenol esters, N-hydroxysuccinimide (NHS) esters, hydroxybezotriazole (HOBt) esters, hydroxyl-7-aza-benzotriazole (HOAt) esters, and the like.

In accordance with embodiments of the invention, the reactive esters for reaction with glycosylamines are bound to solid supports in such a manner that the acyl parts of the active esters will acylate the amino groups on the glycosylamines and become detached from the solid supports. Therefore, the products of the derivatization reactions are acylated glycosylamines that will move with the mobile phase to the next column (shown as the trapping column 25 in FIGS. 2A and 2B).

Figure 3:
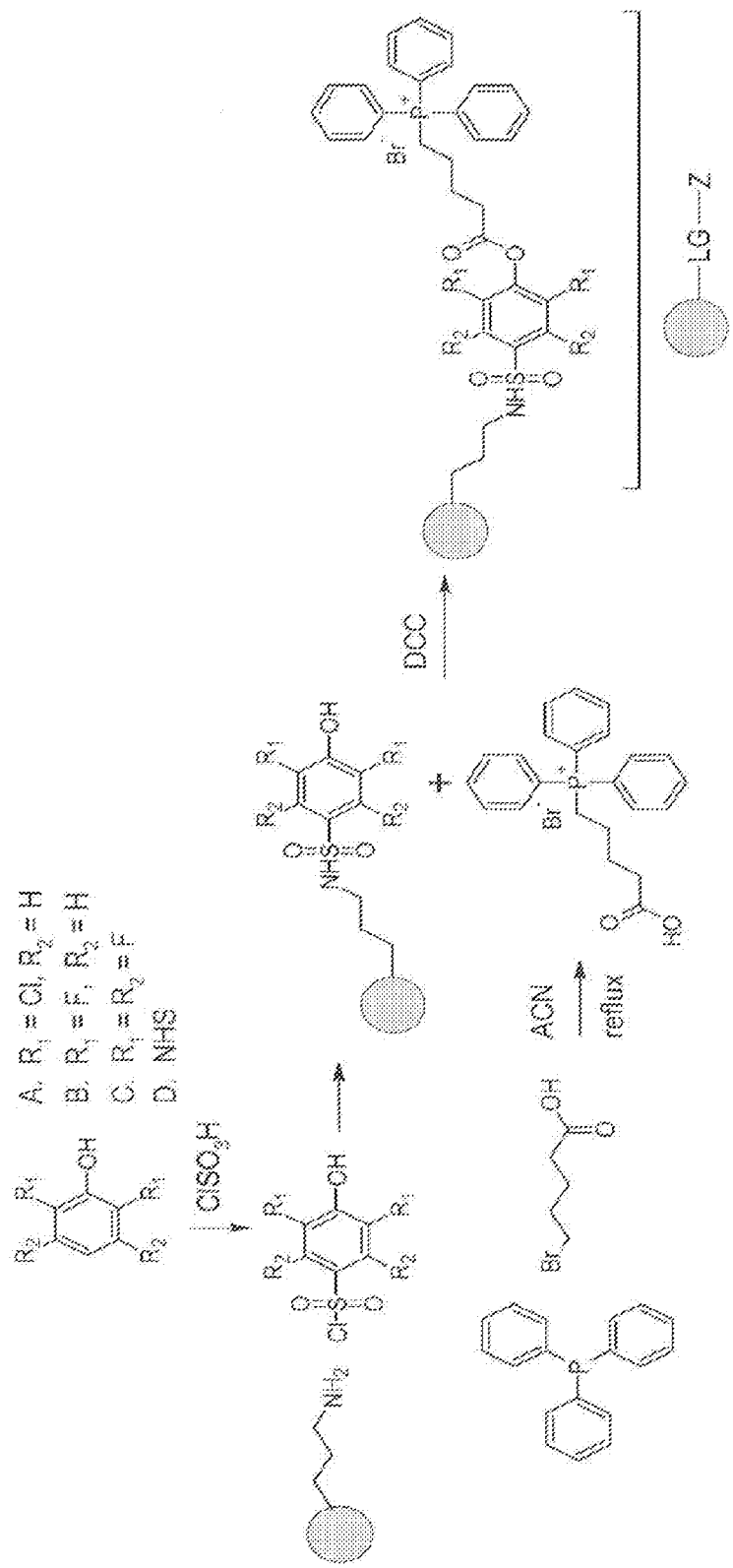
FIG. 3 shows a method of for the preparation of a reactive ester attached to a solid support in accordance with one embodiment of the invention.

FIG. 3 shows an example of an approach to produce an active ester attached to a solid support. This example uses a triphenylphosphonium tag for glycan tagging. A similar triphenylphosphonium tag has been reported by Inagaki et al. to produce a 500-fold increase in MS sensitivity for the derivatized amino acids (Inagaki, S. et al., *Highly sensitive and positively charged precolumn derivatization reagent for amines and amino adds in liquid chromatography/electrospray ionization tandem mass spectrometry*, Rapid Communications in Mass Spectrometry, 2010, 24(9): p. 1358-1364). However, the use of triphenylphosphonium is for illustration only. One skilled in the art would appreciate that other tag moieties may be used without departing from the scope of the invention.

As shown in FIG. 3, a triphenylphosphonium tag may be modified so that it may be attached to a solid phase resin. First, a substituted phenol is sulfonylated at the para position and converted to a sulfonyl chloride, which is then coupled with an amino group on a linker attached to a solid support. The phenol derivative on the solid support is then converted into an ester by acylation with a 5-triphenylphosphonium pentanoic acid, which is prepared by reacting 5-bromopentanoic acid with triphenylphosphine. The acylation may be promoted by a carbodiimide (e.g., dicyclohexyl carbodiimide (DCC)) or other suitable coupling reagents. The reactions conditions for these reactions may follow those reported by Inagaki, S. et al., *Highly sensitive and positively charged precolumn derivatization reagent for amines and amino adds in liquid chromatography/electrospray ionization tandem mass spectrometry*, Rapid Communications in Mass Spectrometry, 2010, 24(9): p. 1358-1364.

The final product of the above reaction is a 5-triphenylphosphonium pentanoic acid phenyl ester, wherein the phenyl group is linked by a sulfonylamide to the solid support. In other words, the triphenylphosphonium tag is conjugated to the solid phase by way of an activated ester leaving group, which remains bound to the solid phase upon exposure of the tagging reagent to a glycosylamine, as shown in FIG. 4.

Figure 4:
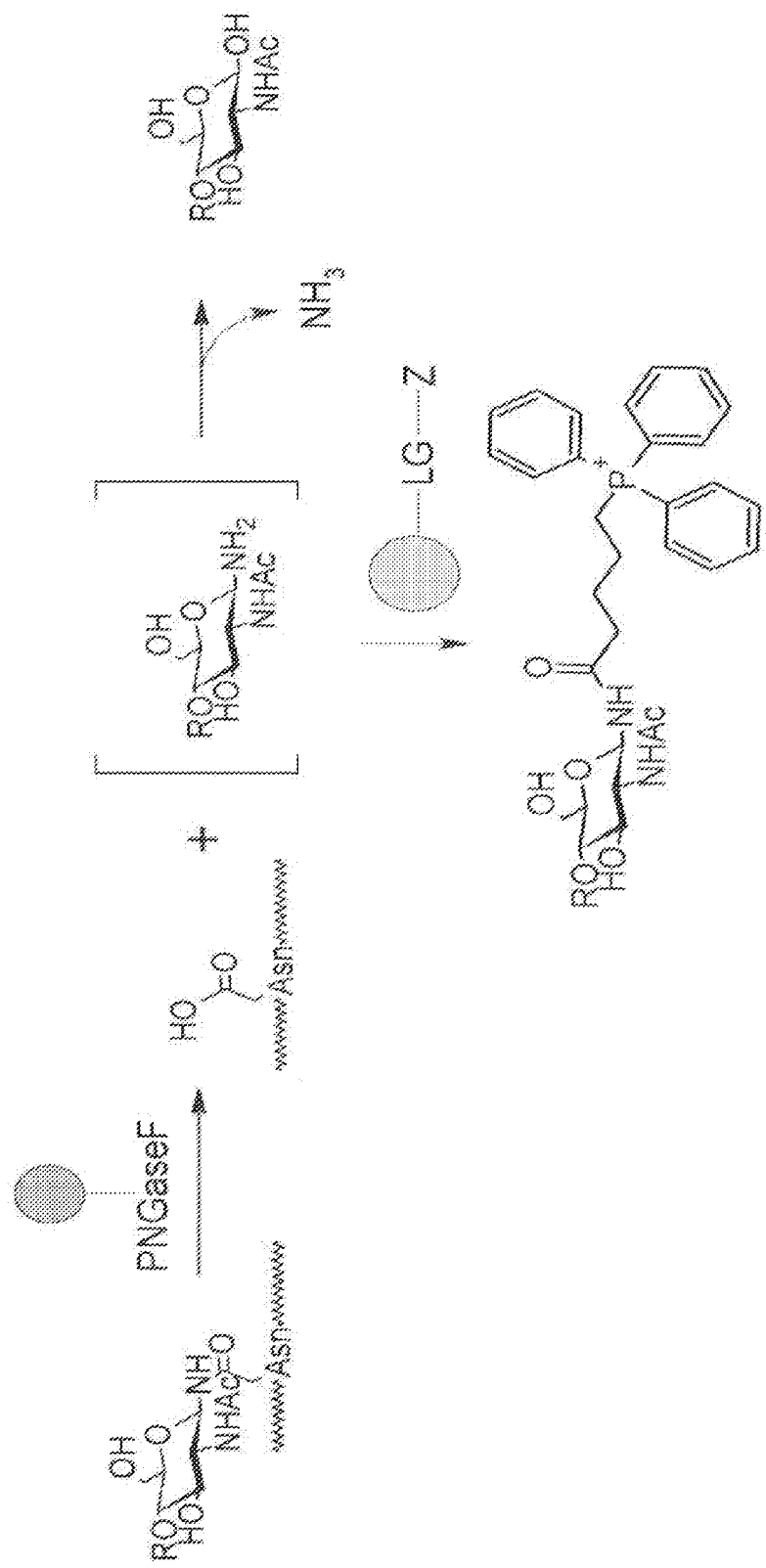
FIG. 4 shows a workflow illustrating deglycosylation followed by derivatization of the produced glycosylamine using an active ester attached to a solid support in accordance with one embodiment of the invention.

As shown in FIG. 4, a glycoprotein may be passed through an enzyme reactor (e.g., a deglycosylation column 22 in FIG. 2A), which contains a PNGase F attached to a solid support. The initial products from the deglycosylation reaction include a glycosylamine, which is reacted in the tagging column (shown as 24 in FIG. 2A) with the activated ester reagent Z that is linked to a solid support via a leaving group (i.e., the phenol ester). The product of the acylation (derivatization) reaction is an acylated glycosylamine. The acyl group in this example is a triphnylphosphonium-pentanoyl group.

Because the "leaving group" (LG) is left bound to the solid phase, the derivatization (tagging) column could be regenerated prior to the next sample analysis to prolong the lifetime of the chip. To reactivate this tagging column, one would simply flow a mixture of the tag and DCC (or a similar coupling agent) through the reaction channel (or reaction column), followed by a thorough wash with a suitable solvent (e.g., acetonitrile).

As shown in FIG. 4, the tagging reagent may be represented as "Z-LG-solid support." The "Z" moiety is eventually attached to the glycosylamine. In accordance with embodiments of the invention, the "Z" moiety (or the tagging group) may be represented as "R—CO—." The R group may be selected to provide the desired properties for the derivatized glycosylamines. For example, the R group may be selected from an alkyl (e.g., $C_1$-$C_{20}$ alkyl, $C_1$-$C_{10}$ alkyl, or $C_1$-$C_4$ alkyl), an alkenyl (e.g., $C_1$-$C_{20}$ alkenyl, $C_1$-$C_{10}$ alkenyl, or $C_1$-$C_4$ alkenyl), an aryl (e.g., $C_6$-$C_{20}$ aryl, $C_6$-$C_{15}$ aryl, or $C_6$-$C_{10}$ aryl), an alkylaryl (wherein the alkyl part and the aryl part are as defined above), a heteroaryl (e.g., $C_3$-$C_{20}$ heteroaryl, $C_3$-$C_{15}$ heteroaryl, or $C_3$-$C_{10}$ heteroaryl), or an alkyl-heteroaryl (wherein the alkyl part and the heteroaryl part are as defined above), wherein each of the alkyl, akenyl, aryl, alkylaryl, heteroaryl, or alkyl-heteroaryl may be optionally substituted with one or more halogen, —OH, —O-alkyl, —$NH_2$, —$NO_2$, —CN, or a $C_1$-$C_6$ alkyl. In preferred embodiments of the invention, the R group comprises a hydrophobic group, such as an aryl, an alkylaryl, a heteroaryl, or an alkyl-heteroaryl group.

The leaving group (LG) comprises a phenol group in the example shown in FIG. 3. Other groups that can form activated esters may also be used with embodiments of the invention. Such other groups, for example, may include hydroxyl-benzotriazole (HOBt), hydroxyl-7-aza-benzotriazole (HOAt), or N-hydroxysuccinimide (NHS), as illustrated in FIG. 5. These groups (HOBt, HOAt, or NHS) can also be made into activated esters with an acyl group by using a coupling agent, such as DCC.

As compared to the existing derivatization workflows, advantages of methods of the invention may include one or more of the following. Embodiments of the invention require decreased sample manipulation and reaction time. As a result, the amounts of starting materials (e.g., micrograms of mAb) needed for accurate glycan profiling are reduced, and minor glycan components may be more easily detected. An additional benefit of the current invention is that the chosen tag significantly alters the chemical nature of the released glycans, which makes quantification of glycans having different chemical properties (such as the number of sialic acid residues that they contain, for example) much more accurate. In other words, the ionization efficiencies of the glycans become more dependent on the tag, which they share in common, rather than on their individual structures. Furthermore, because of the hydrophobic nature of the chosen tags, separation of released glycans using reversed-phase chromatography may be possible, and this separation mode is significantly more robust than the porous graphitized carbon (PGC) chromatography that is currently integrated into the mAb-Glyco-Chip.

Incorporation by Reference

References and citations to other documents, such as patents, patent applications, patent publications, journals, books, papers, web contents, have been made in this disclosure. All such documents are hereby incorporated herein by reference in their entirety for all purposes. Any material, or portion thereof, that is said to be incorporated by reference herein, but which conflicts with existing definitions, statements, or other disclosure material explicitly set forth herein is only incorporated to the extent that no conflict arises between that incorporated material and the present disclosure material. In the event of a conflict, the conflict is to be resolved in favor of the present disclosure as the preferred disclosure.

Equivalents

The representative examples disclosed herein are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples which follow and the references to the scientific and patent literature cited herein. The following examples contain important additional information, exemplification and guidance that can be adapted to the practice of this invention in its various embodiments and equivalents thereof.

What is claimed is:

1. A microfluidic device for glycan analysis, comprising:
   a deglycosylation column comprising a glycosidase attached to a solid support;
   a tagging column comprising a reactive ester for reaction with an amino group of a glucosylamine, wherein the reactive ester is attached to a solid support and the tagging column is arranged downstream of the deglycosylation column;
   an analytical column comprising a stationary phase capable of separating a derivatized glycan; and
   a plurality of inlet/outlet ports configured to connect with channels on a switching element to form flow paths.

2. The microfluidic device of claim 1, wherein the glycosidase is PNGase F.

3. The microfluidic device of claim 1, wherein the glycosidase is PNGase A.

4. The microfluidic device of claim 1, further comprising a clean-up column having a stationary phase capable of binding a protein, wherein the clean-up column is arranged downstream of the deglycosylation column and upstream of the tagging column.

5. The microfluidic device of claim 4, wherein the clean-up column comprises a reversed phase stationary phase.

6. The microfluidic device of claim 1, further comprising a trapping column having a stationary phase capable of binding the derivatized glycan, wherein the trapping column is configured to be connected downstream of the tagging column and upstream of the analytical column.

7. The microfluidic device of claim 6, wherein the trapping column comprises a reversed phase stationary phase.

8. The microfluidic device of claim 1, wherein the analytical column comprises a reversed phase stationary phase.

9. The microfluidic device of claim 8, wherein the reversed phase stationary phase is C-18.

10. A system for analyzing a sample, comprising the microfluidic device of claim 1, a switching device, and a mass spectrometer.

11. A method for glycan analysis using a microfluidic device of claim 1, the method comprising:

applying a sample comprising a glycoprotein to the deglycosylation column on the microfluidic device to produce a deglycosylated mixture;

passing the deglycosylated mixture through the tagging column to produce a derivatized glycosylamine; and separating the derivatized glycosylamine on the analytical column.

12. The method of claim 11, wherein the glycosidase is PNGase F.

13. The method of claim 11, wherein the glycosidase is PNGase A.

14. The method of claim 11, wherein the microfluidic device further comprises a clean-up column having a stationary phase capable of binding a protein, wherein the clean-up column is arranged downstream of the deglycosylation column and upstream of the tagging column, the method further comprising passing the deglycosylated mixture through the clean-up column before the passing the deglycosylated mixture through the tagging column.

15. The method of claim 14, wherein the clean-up column comprises a reversed phase stationary phase.

16. The method of claim 11, wherein the microfluidic device further comprises a trapping column having a stationary phase capable of binding the derivatized glycan, wherein the trapping column is configured to be connected downstream of the tagging column and upstream of the analytical column, the method further comprising passing the derivatized glycan through the trapping column before the separating the derivatized glycosylamine on the analytical column.

17. The method of claim 16, wherein the trapping column comprises a reversed phase stationary phase.

18. The method of claim 11, wherein the analytical column comprises a reversed phase stationary phase.

19. The method of claim 18, wherein the reversed phase stationary phase is C-18.

* * * * *

UNITED STATES PATENT AND TRADEMARK OFFICE
CERTIFICATE OF CORRECTION

PATENT NO. : 8,927,263 B2
APPLICATION NO. : 13/953105
DATED : January 6, 2015
INVENTOR(S) : Brian Phillip Smart et al.

Page 1 of 1

It is certified that error appears in the above-identified patent and that said Letters Patent is hereby corrected as shown below:

In the Claims,

In column 10, line 33, in claim 1, delete "glucosylamine," and insert -- glycosylamine, --, therefore.

Signed and Sealed this
Ninth Day of June, 2015

Michelle K. Lee
*Director of the United States Patent and Trademark Office*